United States Patent
Bahl (12)

(10) Patent No.: US 6,696,486 B1
(45) Date of Patent: Feb. 24, 2004

(54) MEDICAL USE FOR ATYPICAL β-ADRENOCEPTOR AGONISTS

(75) Inventor: Ashwani Kumar Bahl, Ware (GB)

(73) Assignee: Glaxo Group Limited, Greenford (GB)

(*) Notice: Subject to any disclaimer, the term of this patent is extended or adjusted under 35 U.S.C. 154(b) by 1815 days.

(21) Appl. No.: 08/601,442

(22) Filed: Feb. 14, 1996

Related U.S. Application Data

(62) Division of application No. 08/290,522, filed on Jul. 15, 1994, now abandoned, which is a division of application No. 08/006,952, filed on Jan. 21, 1993, now abandoned.

(30) Foreign Application Priority Data

Jan. 22, 1992 (GB) .............................................. 9201359
Dec. 9, 1992 (GB) .............................................. 9225684

(51) Int. Cl.[7] .............................................. A61K 31/36
(52) U.S. Cl. ........................ 514/465; 514/925; 514/926; 514/976

(58) Field of Search ................................. 514/465, 925, 514/926, 976

(56) References Cited

U.S. PATENT DOCUMENTS

| | | | | | |
|---|---|---|---|---|---|
| 5,043,358 | A | * | 8/1991 | Lukacsko et al. | 514/653 |
| 5,071,842 | A | * | 12/1991 | Lukacsko et al. | 514/161 |
| 5,244,923 | A | * | 9/1993 | Holloway et al. | 514/620 |
| 5,260,333 | A | * | 11/1993 | Lukacsko et al. | 514/471 |
| 5,393,779 | A | * | 2/1995 | Holloway et al. | 514/539 |
| 5,434,184 | A | * | 7/1995 | Holloway et al. | 514/567 |

* cited by examiner

*Primary Examiner*—Theodore J. Criares
(74) *Attorney, Agent, or Firm*—Bacon & Thomas

(57) ABSTRACT

The present invention relates to the use of compounds which act as agonists at atypical beta-adrenoceptors, for the treatment of gastrointestinal disorders, especially peptic ulceration, oesophagitis, gastritis and duodenitis, intestinal ulcerations, including inflammatory bowel disease, and gastrointestinal ulcerations, especially when induced by non-steroidal anti-inflammatory drugs or corticosteroids.

7 Claims, No Drawings

MEDICAL USE FOR ATYPICAL β-ADRENOCEPTOR AGONISTS

This application is a division of application Ser. No. 08/290,522, filed Jul. 15, 1994, now abandoned, which is a division of application Ser. No. 08/006,952, filed Jan. 21, 1993, now abandoned.

This invention relates to a new medical use for certain chemical compounds and pharmaceutical compositions containing them. In particular it relates to the use in the treatment of gastrointestinal disorders of compounds which act as agonists at atypical beta-adrenoceptors (also known as beta-3-adrenoceptors). Such receptors have been described for example by J R S Arch et. al., Nature, 309, 163–165 (1984); C Wilson et. al., Eur. J. Pharmacol., 100, 309–319 (1984); L J Emorine et. al., Science, 245, 1118–1121 (1989); and A. Bianchetti et. al. Br. J. Pharmacol., 100, 831–839 (1990).

Atypical beta-adrenoceptors belong to the family of adrenoceptors which mediate the physiological actions of the hormones adrenaline and noradrenaline. Sub-types of the adrenoceptors, $\alpha_1$-, $\alpha_2$-, $\beta_1$-, $\beta_2$- and $\beta_3$-(atypical) can be identified on the basis of their pharmacological properties and physiological effects. Chemical agents which stimulate or block these receptors (but not $\beta_3$) are widely used in clinical medicine. More recently, emphasis has been placed upon specific receptor selectivity in order to reduce side effects caused, in part, by interactions with other receptors.

Atypical beta-adrenoceptors are known to occur in adipose tissue and the gastrointestinal tract. Compounds which act as agonists at atypical beta-adrenoceptors may be identified using standards tests (see for instance C Wilson et. al., supra).

A variety of compounds which act as agonists at atypical beta-adrenoceptors have been described in the art. These compounds are generally N-substituted arylethylamines in which the 2-carbon atom of the ethyl moiety is most commonly substituted by a hydroxy group.

Alternatively the 2-carbon atom may be cyclised via an oxygen atom and a methylene or ethylene linkage to the amine moiety to form oxazolidine or morpholine derivatives. The aryl group is most commonly an optionally substituted phenyl group, but may also be an optionally substituted benzofuranyl, indolyl, pyridinyl or thienyl group.

The N-substituents(s) is/are generally an aralkyl or aralkyloxy substituent in which the aryl group is commonly an optionally substituted phenyl group or an optionally substituted thienyl group.

Atypical beta-adrenoceptor agonists have been found to be particularly useful as thermogenic anti-obesity agents and as anti-diabetic agents.

Compounds having atypical beta-adrenoceptor agonist activity have also been described as being useful in the treatment of hyperglycaemia, as animal growth promoters, as blood platelet aggregation inhibitors, as positive inotropic agents and as antiathereosclerotic agents, and as being useful in the treatment of glaucoma.

It has now been found unexpectedly that compounds which act as agonists at atypical beta-adrenoceptors may be useful for the treatment of gastrointestinal disorders, especially, peptic ulceration, oesophagitis, gastritis and duodenitis (including that induced by *H.pylori*), intestinal ulcerations (including inflammatory bowel disease, especially, ulcerative colitis, Crohn's disease and proctitis) and gastrointestinal ulcerations, especially when induced by non-steroidal anti-inflammatory drugs (NSAIDs) or corticosteroids.

Accordingly the present invention provides a method of treatment of a mammal, including man, suffering from a gastrointestinal disorder, such as peptic ulceration, oesophagitis, gastritis, duodenitis, intestinal ulcerations and gastrointestinal ulcerations, which comprises administering to the subject an effective amount of a compound which acts as an agonist at atypical beta-adrenoceptors.

In a preferred aspect of the present invention, there is provided a method of treatment of a mammal, including man, suffering from a condition of intestinal ulcerations wherein said condition is an inflammatory bowel disease, such as ulcerative colitis, Crohn's disease or proctitis, which comprises administering to the subject an effective amount of a compound which acts as an agonist at atypical beta-adrenoceptors.

In a particularly preferred aspect of the present invention, there is provided a method of treatment of a mammal, including man, suffering from a condition of gastrointestinal ulcerations wherein said condition is induced by non-steroidal anti-inflammatory drugs, which comprises administering to the subject an effective amount of a compound which acts as an agonist at atypical beta-adrenoceptors.

References in this specification to treatment include prophylactic treatment as well as the acute alleviation of symptoms.

Preferred compounds for use according to the invention are those compounds which act as agonists at atypical beta-adrenoceptors described in published European Patent Specification Nos. 6735, 21636, 23385, 25331, 28105, 29320, 40000, 40915, 51917, 52963, 61907, 63004, 66351, 68669, 70133, 70134, 82665, 89154, 91749, 94595, 95827, 99707, 101069, 102213, 139921, 140243, 140359, 142102, 146392, 164700, 170121, 170135, 171519, 171702, 182533, 185814, 196849, 198412, 210849, 211721, 233686, 236624, 254532, 254856, 262785, 300290, 303546, 328251, 345591, 386603, 386920, 436435, 455006 and 500443; published UK Patent Specification No. 2133986; published PCT Patent Specification Nos. 84/00956, 84/03278, 84/04091, 90/13535 and 92/18461; U.S. Pat. Nos. 4,391,826 and 4,585,796; published Belgian Patent Specification No. 900983 and published Japanese Patent Specification No.86-145148.

A preferred group of atypical beta-adrenoceptor agonists for use according to the present invention is that represented by the formula (I):

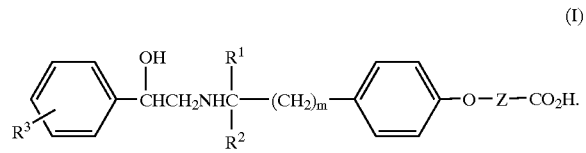

(I)

or a physiologically acceptable salt, ester or amide thereof, wherein $R^1$ and $R^2$ each independently represent a hydrogen atom or a methyl group;

$R^3$ represents a hydrogen, fluorine or chlorine atom or a trifluoromethyl group;

Z is an alkylene, alkenylene or alkynylene group of up to 10 carbon atoms; and m is 1, 2 or 3.

Another preferred group of atypical beta-adrenoceptor agonists for use according to the present invention is that represented by the formula (II):

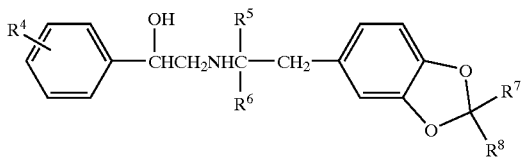

(II)

or a physiologically acceptable salt or ester thereof, wherein
$R^4$ represents one or more groups which may be the same or different and are selected from the group consisting of hydrogen, halogen, trifluoromethyl, $C_{1-4}$alkyl, $C_{1-4}$alkoxy, $C_{1-4}$alkylthio, alkoxycarbonyl, carboxyl, hydroxyalkyl, hydroxy, $C_{1-4}$alkylsulphonyl and $C_{1-4}$alkylsulphinyl;

$R^5$ and $R^6$ each independently represent a hydrogen atom or a $C_{1-4}$alkyl group;

$R^7$ and $R^8$ each independently represent a group selected from the group consisting of hydrogen, carboxy, alkoxycarbonyl, hydroxymethyl, $—CH_2OCH_2CO_2R^9$ and $—CH_2OCH_2CH_2OR^9$, with the proviso that $R^7$ and $R^8$ do not both represent hydrogen; and $R^9$ is a hydrogen atom or a $C_{1-4}$alkyl group.

A yet further preferred group of atypical beta-adrenoceptor agonists for use according to the present invention is that represented by the formula (III):

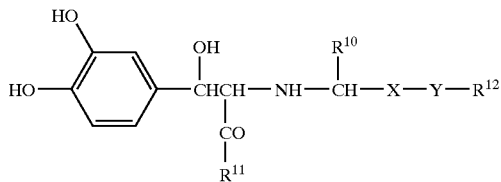

(III)

or a physiologically acceptable salt thereof, wherein
$R^{10}$ represents a hydrogen atom or a $C_{1-4}$ alkyl or a phenyl group;

$R^{11}$ represents a group of the formula $—OR^{13}$ or $—NR^{14}R^{15}$;

$R^{12}$ represents a group selected from $C_{1-3}$alkyl, cyclohexyl, phenyl (optionally substituted by one or more groups selected from $C_{1-4}$alkyl, hydroxy, methoxy, dimethylamino, trifluoromethyl, methylenedioxy or halogen atoms), naphthyl, pyridyl, furyl, thienyl or pyrrolyl;

$R^{13}$ represents a $C_{1-4}$alkyl or carbo$C_{1-2}$alkoxymethyl group;

$R^{14}$ represents a hydrogen atom or a methyl, ethyl or amino group;

$R^{15}$ represents a hydrogen atom or methyl group; or the group $—NR^{14}R^{15}$ form a cyclic amino group of the formula

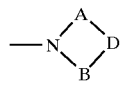

wherein A and B each independently represent a single bond or an unsubstituted straight $C_{1-3}$alkylene chain, or a straight $C_{1-3}$alkylene chain substituted by carbomethoxy, hydroxymethyl or phenyl, and D is methylene, ethylene, 1,2-cyclohexylidine or 1,2-benzo;

X is a single bond or a straight $C_{1-4}$alkylene chain; and
Y is a single bond, oxa, methylimino or $—CONH—$;
or $R^{10}—CH—X—Y—R^{12}$ forms a tetrahydronaphthyl group.

Yet another preferred group of atypical beta-adrenoceptor agonists for use according to the present invention is that represented by the formula (IV):

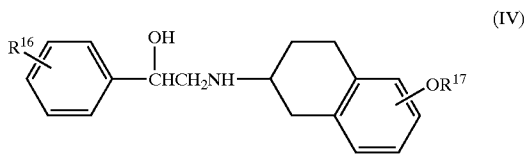

(IV)

or a physiologically acceptable salt thereof, wherein
$R^{16}$ represents a hydrogen or a halogen atom or a trifluoromethyl or $C_{1-4}$alkyl group; and $R^{17}$ represents a hydrogen atom or a group selected from $C_{1-4}$alkyl (optionally substituted by a $C_{3-7}$cycloalkyl, hydroxy, $C_{1-4}$alkoxy, carboxy or $C_{1-4}$alkoxycarbonyl group), $C_{3-7}$cycloalkyl or $C_{1-4}$alkanoyl.

Particularly preferred atypical beta-adrenoceptor agonists and physiologically acceptable salts or solvates thereof for use according to the present invention are listed below. It will be appreciated that where the above compounds of formulae (I) to (IV) and the following specific compounds are optically active, the use of individual enantiomers, diastereoisomers or mixtures thereof, including racemates, is also considered to be within the scope of the present invention.

N-[2-(4-carbomethoxymethoxyphenyl)-1-methylethyl]-2-hydroxy-2-(3-chloropheny)ethanamine (BRL 35135);

N-[2-(4-carboxymethoxyphenyl)-1-methylethyl]-2-hydroxy-2-(3-chlorophenyl)ethanamine (BRL 37344);

DL-threo-3-(3,4-dihydroxyphenyl)-N-(3-(4-fluorophenyl)propyl)serine pyrrolidine amide (SM-1 1044);

5,6,7,8-tetrahydro-7-[(2-hydroxy-2-phenylethyl)amino]-2-naphthalenol (SR-58306);

2-[[7-ethoxycarbonylmethoxy-1,2,3,4-tetrahydronaphth-2-yl]amino]-1-[3-chlorophenyl]ethanol (SR-58380);

7-[[2-(3-chlorophenyl)-2-hydroxyethyl]amino]-5,6,7,8-tetrahydro-2-naphthalenol (SR-58572);

N-[(2S)-7-ethoxycarbonylmethoxy-1,2,3,4-tetrahydronaphth-2-yl]-(2R)-2-(3-chlorophenyl)-2-hydroxyethanamine (SR-58611);

N-[[7-carboxymethyl]-1,2,3,4-tetrahydronaphth-2-yl]-2-hydroxy-2-(3-chlorophenyl)ethylamine (SR-58398);

(R,R)-5-(2-((2-(3-chlorophenyl)-2-hydroxyethyl)amino) propyl)-1,3-benzodioxole-2,2-dicarboxylic acid (CL-316243), particularly in the form of its disodium salt;

(R,R)-5-(2-((2-(3-chlorophenyl)-2-hydroxyethyl)amino) propyl)-1,3-benzodioxole-2,2-dicarboxylic acid, dimethyl ester;

(R,R)-5-(2-((2-(3-chlorophenyl)-2-hydroxyethyl)amino) propyl)-1,3-benzodioxole-2,2-dicarboxylic acid, diethyl ester;

(R,R)-(2-((2-(3-chlorophenyl)-2-hydroxyethyl)amino) propyl)-1,3-benzodioxole-2,2-dicarboxylic acid, disopropyl ester;

(R,S)-5-(2-((2-(3-chlorophenyl)-2-hydroxyethyl)amino)
propyl)-1,3-benzodioxole-2,2-carboxylic acid.

In a further aspect, the present invention provides a therapeutic agent which comprises an effective amount of a compound which acts as an agonist at atypical beta-adrenoceptors for use in medicine, particularly human medicine, for the treatment of gastrointestinal disorders such as peptic ulceration, oesophagitis, gastritis, duodenitis, intestinal ulcerations and gastrointestinal ulcerations.

In a further preferred aspect of the present invention, there is provided a therapeutic agent which comprises an effective amount of a compound which acts as an agonist at atypical beta-adrenoceptors for use in the treatment of a condition of intestinal ulcerations wherein said condition is an inflammatory bowel disease such as ulcerative colitis, Crohn's disease or proctitis.

In a further particularly preferred aspect of the present invention, there is provided a therapeutic agent which comprises an effective amount of a compound which acts as an agonist at atypical beta-adrenoceptors for use in the treatment of a condition of gastrointestinal ulcerations wherein said condition is induced by non-steroidal anti-inflammatory drugs.

In a yet further aspect, the invention provides for the use of a compound which acts as an agonist at atypical beta-adrenoceptors, for the manufacture of a medicament for the treatment of gastrointestinal disorders such as peptic ulceration, gastritis, duodenitis, intestinal ulcerations and gastrointestinal ulcerations.

In a yet further preferred aspect of the present invention, there is provided the use of a compound which acts as an agonist at atypical beta-adrenoceptors, for the manufacture of a medicament for the treatment of a condition of intestinal ulcerations wherein said condition is an inflammatory bowel disease such as ulcerative colitis, Crohn's disease or proctitis.

In a yet further particularly preferred aspect of the present invention, there is provided the use of compound which acts as an agonist at atypical beta-adrenoceptors, for the manufacture of a medicament for the treatment of a condition of gastrointestinal ulcerations wherein said condition is induced by non-steroidal anti-inflammatory drugs.

It will be appreciated that where a compound which acts as an agonist at atypical beta-adrenoceptors is used for the treatment of a condition of gastrointestinal ulcerations induced by non-steroidal anti-inflammatory drugs (NSAID's) it may be preferable to co-adminster the atypical beta-adrenoceptor agonist and the NSAID. The active ingredients may be employed in the form of separate pharmaceutical formulations or a combined formulation may be used. In such a combined formulation, the active ingredients must of course be stable and mutually compatible in the particular formulation employed.

Pharmaceutical compositions which comprise at least one compound which acts as an agonist at atypical beta-adrenoceptors and at least one non-steroidal anti-inflammatory drug, together with at least one physiologically acceptable carrier or excipient are believed to be novel compositions and constitute a further asepct of the present invention.

It will be appreciated that similar combined formulations may be utilised for the treatment of a condition of gastrointestinal ulcerations induced by corticosteroids.

Pharmaceutical compositions for use in accordance with the present invention may be formulated in conventional manner using one or more physiologically acceptable carriers or excipients.

Thus the compounds for use according to the present invention may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for use according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds for use according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds for use according to the invention may be formulated with suitable polymeric or hydrophobic materials (for example as an emulsion in an acceptable oil) or ion exchange resins, or as sparingly soluble derivatives, for example, as a sparingly soluble salt.

A proposed dose of the compounds for use according to the invention for administration to a human (of approximately 70 kg body weight) is 0.1 mg to 1 g, preferably to 1 mg to 100 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

Atypical beta-adrenoceptor agonists are compounds which demonstrate a pharmacological response (in vitro or in vivo) mediated at atypical beta-adrenoceptors. This activity has been be measured as the ability to stimulate lipolysis by rat adipocytes at sub-micromolar concentrations, in a response that is resistant to blockade by standard beta-adrenoceptor blocking drugs such as propranolol.

A particularly useful means of identifying an "atypical beta-adrenoceptor agonist" for use in the present invention involves the measurement of agonist activity at atypical beta-adrenoceptors in the rat isolated lower oesophagus. An active compound for use in the present invention is defined as being a compound which has agonist activity in the rat oesophagus assay described below. Typically in this assay, a compound for use in the present invention has an equipotent molar ratio (EPMR) relevant to isoprenaline of less than 30.

The rat oesophagus assay is based upon that described by Ford et. al., *Br. J. Phrmacol.*, 105(suppl.), 235P, 1992, the method of which is described below as Method 1:

Method 1

The lower oesophagus is removed from male AH/A rats (100–150 g), the overlying serosal muscle is removed from the oesophagus to leave the tunis muscularis mucosa. Tissues are then placed in Kreb's solution containing the $\beta_2$-antagonist ICI 118,551 ($10^{-6}$M), the $\beta_1$-antagonist atenolol ($10^{-5}$M), the phosphodiesterase inhibitor isobutyl methyl xanthine (IBMX; $3\times10^{-6}$M) and the prostaglandin synthesis inhibitor indomethacin (3×10–6M), and the tissues suspended under a resting tension of 0.5 g.

Subsequently, tissues are contracted with a submaximal concentration of carbachol ($10^{-6}$M) and, when a stable increase in tension has been achieved, a cumulative concentration effect curve to isoprenaline is constructed. Following washout with fresh Kreb's solution, tissues are recontracted with carbachol ($10^{-6}$M) and a cumulative concentration effect curve to test agonist is constructed.

The relative potency of each test agonist (EPMR) is compared to isoprenaline as follows:

$$EPMR = \frac{EC_{50} \text{ agonist}}{EC_{50} \text{ isoprenaline}}$$

wherein $EC_{50}$ is the molar concentration of agonist which produces 50% of the maximum possible response for that agonist Using the non-selective beta-adrenoceptor agonist isoprenaline as a reference agonist, compounds selective for atypical beta-adrenoceptors should preferably be a minimum of 10–30 times less potent than isoprenaline at $\beta_1$- or $\beta_2$-adrenoceptors and, more preferably, 300–1000 times less potent than isoprenaline at $\beta_1$- or $\beta_2$-adrenoceptors An experimental model in which atypical beta-adrenoceptor agonists may be shown to be of use in the treatment of gastrointestinal disorders is described below as Method 2. The procedure is based upon that described by H. Satoh et. al., Gastroenterology, 81, 719–725 (1981) in which the effect of compounds on indomethacin-induced gastric antral lesions in the re-fed rat is investigated. Indomethacin is an example of the class of compound known as non-steroidal anti-inflammatory drugs (NSAIDs), the use of which is frequently associated with gastrointestinal ulcers.

Method 2

Food (but not water) is withheld from female random hooded rats (70–120 g) for 24 hours and then the rats are re-fed with Rat and Mouse No. 1 Maintenance Diet. After 1 hour of access to food, the rats are dosed orally with either the test compound or solvent (0.5% w/v methyl cellulose in water). 30 minutes later, indomethacin (60 mg/kg; dissolved in 1% w/v $NaHCO_3$ in saline) is administered as a single subcutaneous injection at the back of the neck. Subsequently, the rats are allowed food, but water is withheld, and the animals are humanely killed by cervical dislocation at 6 hours post dose. Control animals received a single subcutaneous dose of the appropriate solvent.

The rat's stomach is removed (with a small amount of duodenum attached), opened along the greater curvature and the contents removed by washing with 0.9% w/v sodium chloride solution (saline). The opened stomach is pinned out (mucosal surface uppermost) on a polystyrene mat and the area of damage assessed by placing a grid (composed of 1 mm squares) over the antral region. Antral damage appears as discrete black or dark brown ulcers. The total area of antral damage is then expressed as a percentage of the total surface area of the antrum.

The protective effect of the test compound on indomethacin-induced antral damage is calculated as a percentage using the following equation:

$$100 \times \left[ \frac{\% \text{ area of damage with } NSAID - \% \text{ area of damage with } NSAID + \text{test compound}}{\% \text{ area of damage with } NSAID} \right]$$

Results

The gastro-protective effects of N-[2-(4-carbomethoxymethoxyphenyl)-1-methylethyl]-2-hydroxy-2-(3-chlorophenyl)ethanamine (BRL 35135) administered as a single dose 30 minutes before indomethacin, is shown by the following data:

| Test compound | Dose (µg/kg p.o.) | % Protection |
|---|---|---|
| BRL 35135 | 20 | 40 |
|  | 50 | 48 |
|  | 100 | 88 |
|  | 500 | 97 |

As can be seen from the above data, the atypical beta-adrenoceptor agonist, BRL35135, had an $ED_{50}$ of approximately 50 µg/kg p.o.

In addition, the active (S)-isomer of the beta-adrenoceptor blocker propranolol (10 mg/kg i.p.) had no effect on the responses of BRL35135.

Further results for individual isomers of BRL35135 as well as other atypical beta-adrenoceptor agonists have been generated demonstrating the compounds' gastro-protective activity in the above assay. The results are shown in Table 1.

The compound (R,R)-5-(2-((2-(3-chlorophenyl)-2-hydroxyethyl) amino)propyl)-1,3-benzodioxole-2,2- dicarboxylic acid (CL 316243) was also tested in the above assay using piroxicam as the non-steroidal anti-inflammatory drug. Indomethacin and piroxicam caused similar amounts of antral damage in this model. At a subcutaneous dose of 60 mg/kg indomethacin gave a percentage area of damage of 19±5% whilst piroxicam (at the same dose) gave 21±3% antral damage.

Pre-treatments with CL 316243, administered as a single dose 30 minutes before NSAID, gave the following data:

| Test compound | Dose (mg/kg p.o.) | % inhibition of indomethacin-induced damage | % inhibition of piroxicam-induced damage |
|---|---|---|---|
| CL 316243 | 0.5 | 83 | 96 |

Another experimental model in which atypical beta-adrenocopter agonists may be shown to be of use in the treatment of gastrointestinal disorders is described below as Method 3. This is a model of indomethacin-induced ulceration of the small intestine in the rat.

Method 3

Female random hooded rats (100–150 g) are allowed free access to food and water. The rats are dosed orally with either the test compound (1 ml per 100 g of an appropriated dose) or solvent (0.5% w/v methyl cellulose in water). 30 minutes later, indomethacin (15 mg/kg) is administered orally using a dose volume of 1 ml per 100 g of a 1.5 mg/ml solution of indomethacin in 1% w/v $NaHCO_3$. The animals are humanely killed by cervical dislocation at 48 hours post dose.

The rat's small intestine is removed, opened along its length and the contents removed by washing with 0.9% w/v sodium chloride solution (saline). The opened small intestine is pinned out (mucosal surface uppermost) on a polystyrene mat and the area of damage assessed by placing a grid (composed of 1 mm squares) over the preparation. The number of visible ulcers (appearing as discrete black or brown lesions) running the length of the small intestine is counted. The protective effect of the test compound is calculated as a percentage using the following equation:

$$100 \times \left[ \frac{\text{number of visible ulcers with indomethacin} - \text{number of visible ulcers with indomethacin + test compound}}{\text{number of visible ulcers with indomethacin}} \right]$$

Results

Inhibition of indomethacin-induced ulceration of the rat small intestine with N-[2-(4-carbomethoxymethoxyphenyl)-1-methylethyl]-2-hydroxy-2-(3-chlorophenyl)ethanamine (BRL 35135) or (R,R)-5-(2-((2-(3-chlorophenyl)-2-hydroxyethyl)amino)propyl)-1,3-benzodioxole-2,2-dicarboxylic acid (CL 316243), each administered as a single dose 30 minutes before indomethacin, is shown by the following data:

| Test Compound | Dose (mg/kg p.o.) | % inhibition |
|---|---|---|
| BRL 35135 | 10 | 80 ± 3 |
| (n = 7) | 2.5 | 85 ± 3 |
|  | 0.5 | 76 ± 3 |
|  | 0.1 | 35 ± 7 |
|  | 0.05 | 24 ± 15 |
| CL 316243 | 10 | 93 ± 4 |
| (n = 6) |  |  |

The following examples illustrate pharmaceutical formulations for use according to the invention, containing an agonist of atypical beta-adrenoceptors.

TABLETS FOR ORAL ADMINISTRATION

Tablets may be prepared by the normal methods such as direct compression or wet granulation.

The tablets may be film coated with suitable film forming materials, such as hydroxypropyl methylceilulose, using standard techniques. Alternatively the tablets may be sugar coated.

Direct Compression Tablet

|  |  | mg/tablet |
|---|---|---|
| (i) | Active Ingredient | 4.688 |
|  | Calcium Hydrogen Phosphate BP* | 83.06 |
|  | Croscarmellose Sodium NF | 1.8 |
|  | Magnesium Stearate BP | 0.45 |
|  | Compression weight | 90.0 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

|  |  | mg/tablet |
|---|---|---|
| (ii) | Active Ingredient | 0.31 |
|  | Anhydrous Lactose USNF | 131.99 |
|  | Pregelatinised Starch USNF | 7.0 |
|  | Magnesium Stearate BP | 0.7 |
|  | Compression weight | 140.0 |

The active ingredient is passed through a 60 mesh sieve, and blended with the lactose, pregelatinised starch and magnesium stearate. The resultant mix is compressed into tablets using a Manesty F3 tablet machine fitted with 7.5 mm normal concave punches.

SYRUP

This may be either a sucrose or sucrose free presentation.

| A. | Sucrose Syrup | mg/5 ml dose |
|---|---|---|
| | Active Ingredient | 2.5 |
| | Sucrose BP | 2750.0 |
| | Glycerine BP | 500.0 |
| | Buffer ) | |
| | Flavour ) | |
| | Colour ) | as required |
| | Preservative ) | |
| | Purified Water BP to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. | Sucrose-free Syrup | mg/5 ml dose |
|---|---|---|
| | Active Ingredient | 2.5 |
| | Hydroxypropylmethylcellulose USP (viscosity type 4000) | 22.5 |
| | Buffer ) | |
| | Flavour ) | |
| | Colour ) | as required |
| | Preservative ) | |
| | Sweetener ) | |
| | Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

INJECTION FOR INTRAVENOUS ADMINISTRATION

| | | µg/ml |
|---|---|---|
| (i) | Active Ingredient | 800 |
| | Dilute Hydrochloric Acid BP to pH | 3.5 |
| | Sodium Chloride Injection BP to | 1 ml |

The active ingredient is dissolved in a suitable volume of Sodium Chloride Injection BP, the pH of the resultant solution is adjusted to pH3.5 with dilute hydrochloric acid BP then the solution is made to volume with sodium chloride injection BP and thoroughly mixed. The solution is filled into Type 1 clear glass 5 ml ampoules which are sealed under a headspace of air, by fusion of the glass then sterilised by autoclaving at 120° for not less than 15 minutes.

| | | µg/ml |
|---|---|---|
| (ii) | Active ingredient | 56.2 |
| | Sodium Chloride BP | as required |
| | Water for Injection BP to | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

SUPPOSITORY FOR RECTAL ADMINISTRATION

| Active ingredient | 49.0 mg |
|---|---|
| Witepsol* H15 to | 1.0 g |

*a proprietary grade of Adeps Solidus Ph. Eur.

A suspension of the active ingredient in molten Witepsol is prepared and filled using suitable machinery, into 1 g size suppository moulds.

TABLE 1

| | In vivo activity (inhibition of indomethacin-induced antral ulceration in rat) | | |
|---|---|---|---|
| Test Compound | $ED_{50}$ (mg/kg p.o.) | Maximum Inhibition (dose; mg/kg p.o.) | Effect of propranolol (10 mg/kg i.p.) |
| (R,R)-N-[2-(4-carbo-methoxymethoxyphenyl)-1-methylethyl]-2-hydroxy-2-(3-chlorophenyl)ethanamine | 0.02 | 100% (3) | NSE |
| (R,S)-N-[2-(4-carbo-methoxymethoxyphenyl)-1-methylethyl]-2-hydroxy-2-(3-chlorophenyl)ethanamine | 0.2 | 93% (3) | NT |
| (S,R)-N-[2-(4-carbo-methoxymethoxyphenyl)-1-methylethyl]-2-hydroxy-2-(3-chlorophenyl)ethanamine | 0.5 | 88% (3) | NT |
| (R,R)-N-[2-(4-carboxy-methoxyphenyl)-1-methyl-ethyl]-2-hydroxy-2-(3-chlorophenyl)ethanamine | 0.03 | 100% (3) | NSE |
| (R,S)-N-[2-(4-carboxy-methoxyphenyl)-1-methyl-ethyl]-2-hydroxy-2-(3-chlorophenyl)ethanamine | 0.3 | 77% (3) | NSE |
| (S,S)-N-[2-(4-carboxy-methoxyphenyl)-1-methyl-ethyl]-2-hydroxy-2-(3-chlorophenyl)ethanamine | 0.8 | 97% (3) | NT |

TABLE 1-continued

| | In vivo activity (inhibition of indomethacin-induced antral ulceration in rat) | | |
|---|---|---|---|
| Test Compound | $ED_{50}$ (mg/kg p.o.) | Maximum Inhibition (dose; mg/kg p.o.) | Effect of propranolol (10 mg/kg i.p.) |
| (R,R)-5-(2-((2-(3-chloro-phenyl)-2-hydroxyethyl)-amino)propyl)-1,3-benzo-dioxole-2,2-dicarboxylic acid | 0.03 | 96% (1) | NSE |
| (R,S)-5-(2-((2-(3-chloro-phenyl)-2-hydroxyethyl)-amino)propyl)-1,3-benzo-dioxole-2,2-dicarboxylic acid | 0.6 | 64% (1) | NT |

NSE = no significant effect
NT = not tested

I claim:

1. A method of treatment of a human or non-human mammalian subject suffering from gastrointestinal disease which is oesophagitis, gastritis, or duodenitis, which comprises administering to the subject an effective amount of a compound which acts as an agonist at and is selective for atypical beta-adrenoceptors.

2. A method according to claim 1 wherein said compound is administered in the form of a medicament adapted for oral, buccal, parenteral, rectal or transdermal administration or in a form for administration by inhalation or insufflation.

3. A method according to claim 1 wherein said compound is administered in the form of a medicament in unit dose form containing from 0.1 mg to 1 g of active ingredient per unit dose, expressed as the weight of free base.

4. A method according to claim 3 wherein the amount of active ingredient per unit dose is from 1 mg to 100 mg.

5. A method according to claim 1 wherein the gastrointestinal disease is oesophagitis.

6. A method according to claim 1 wherein the gastrointestinal disease is gastritis.

7. A method according to claim 1 wherein the gastrointestinal disease is duodenitis.

* * * * *